United States Patent [19]
Vértesy et al.

[11] Patent Number: 6,077,830
[45] Date of Patent: Jun. 20, 2000

[54] BISMUTH SALTS OF ANTIBIOTICS OF THE MOENOMYCIN GROUP, PROCESSES FOR THEIR PREPARATION, THEIR USE AND PHARMACEUTICALS COMPRISING SUCH SALTS

[75] Inventors: Laszló Vértesy, Eppstein; Michael Kurz, Hofheim; Astrid Markus, Liederbach; Gerhard Seibert, Darmstadt, all of Germany

[73] Assignee: Hoechst Aktiengesellschaft, Frankfurt am Main, Germany

[21] Appl. No.: 09/036,683

[22] Filed: Mar. 9, 1998

[30] Foreign Application Priority Data

Mar. 11, 1997 [DE] Germany ............... 197 09 897

[51] Int. Cl.$^7$ .................................................. A61K 31/70
[52] U.S. Cl. .................... 514/25; 514/53; 536/16.8; 536/17.2; 536/117
[58] Field of Search ............ 514/25, 53; 536/16.8, 536/17.2, 117, 53

[56] References Cited

U.S. PATENT DOCUMENTS

| | | |
|---|---|---|
| 3,992,263 | 11/1976 | Dietrich et al. . |
| 5,206,405 | 4/1993 | Aretz et al. . |
| 5,260,206 | 11/1993 | Aretz et al. . |
| 5,315,038 | 5/1994 | Aretz et al. . |
| 5,506,140 | 4/1996 | Aretz et al. . |

FOREIGN PATENT DOCUMENTS

| | | |
|---|---|---|
| 0 355 679 A3 | 2/1990 | European Pat. Off. . |
| 0 652 205 A2 | 5/1995 | European Pat. Off. . |
| 0 655 249 A1 | 5/1995 | European Pat. Off. . |

OTHER PUBLICATIONS

Axon, A. T. R., "*Helicobacter pylori* infection," *Journal of Antimicrobial Chemotherapy*, vol. 32, Suppl. A, pp. 61–68 (1993).

Beil, W. And Birkholz, C., "Colloidal Bismuth Subcitrate and Omeprazole Inhibit *Helicobacter pylori* F$_1$–Atpase," *Archives of Pharmacology*, vol. 350, p. R1 (1994).

English language abstract of EP 0 655 249 A1 (Derwent Abstract No. 95–195396).

Hessler–Klintz, Martina et al., "The First Moenomycin Antibiotic Without the Methyl–Branched Uronic Acid Consititutent.–Unexpected Structure Activity Relations," *Tetrahedron*, vol. 49, pp. 7667–7678 (1993).

Huber, Gerhard, "Moenomycin and Related Phosphorus–Containing Antibotics," *Archives of Pharmacology*, vol. 350, pp. 135–153 (1994).

Walsh, John H., "The Treatment of *Helicobacter pylori* Infection in the Management of Peptic Ulcer Disease," *The New England Journal of Medicine*, vol. 333, No. 15, pp. 984–991 (Oct. 12, 1995).

English language abstract of 0 355 679 A3 (ESPACE Abstract No. 90/009FIRST 90/001).

English language abstract of 0 652 205 A2 (ESPACE Abstract No. 95/032FIRST 95/003).

G. Huber; "Moenomycin and Related Phosphorus–Containing Antibiotics", Antibiotics, vol. V/Part 1, pp. 135–153, (1979).

M. Hessler–Klintz et al.; "The First Moenomycin Antibiotic Without the Methyl–Branched Uronic Acid Constituent. –Unexpected Structure Activity Relations", Tetrahedron, vol. 49, No. 35, pp. 7667–7678, (1993).

*Primary Examiner*—Elli Peselev
*Attorney, Agent, or Firm*—Finnegan, Henderson, Farabow, Garrett & Dunner, L.L.P.

[57] ABSTRACT

The present invention relates to bismuth salts of antibiotics of the moenomycin group, processes for their preparation, their use and pharmaceuticals comprising such salts. The salts according to the invention contain antibiotics of the moenomycin group which are so-called phosphoglycolipid antibiotics and which are present individually or as a mixture, or derivatives thereof, and bismuth in defined stoichiometric ratios. They are outstandingly suitable, in particular, for controlling *Helicobacter pylori* and, thus, for example, for the therapy and prophylaxis of gastric disorders.

18 Claims, No Drawings

BISMUTH SALTS OF ANTIBIOTICS OF THE MOENOMYCIN GROUP, PROCESSES FOR THEIR PREPARATION, THEIR USE AND PHARMACEUTICALS COMPRISING SUCH SALTS

The present invention relates to bismuth salts of antibiotics of the moenomycin group, processes for their preparation, their use and pharmaceuticals comprising such salts. The salts according to the invention contain antibiotics of the moenomycin group which are so-called phosphoglycolipid antibiotics and which are present individually or as a mixture, or derivatives thereof, and bismuth in defined stoichiometric ratios. They are outstandingly suitable, in particular, for controlling *Helicobacter pylori* and, thus, for example, for the therapy and prophylaxis of gastric disorders.

For the treatment and prevention of gastric ulcers or gastritis and also for the prophylaxis of stomach cancer, hitherto especially so-called antacids and, with particular success, $H_2$ receptor blockers have been used. Meanwhile, it has been recognized that infections with the microorganism *Helicobacter pylori* are frequently responsible for gastric disorders such as, for example, gastric ulcers (see, for example, A. T. R. Axon, "*Helicobacter pylori* Infection", *J. Antimicrob. Chemother.* 32, Suppl. A, 61, 1993). The infection of the human stomach with the pathogenic gram-negative bacterium *Helicobacter pylori* causes temporary dyspeptic symptoms, but the microorganism has a high persistence. *H. pylori* is moreover the underlying pathogen in the chronically active type b gastritis and a significant risk factor for the occurrence of stomach cancer. The pathophysiological mechanisms by which *H. pylori* causes diseases of the stomach are still relatively unclear. It is known that the microorganism produces a number of potentially toxic enzymes and chemicals (urease, ammonia, vacuolizing cytotoxin). The persistence of the harmful bacterium and the lasting antigenic stimulus are probably causal for the destruction of the gastric mucous membrane which takes place long-term.

The therapeutic aim is the complete eradication of *H. pylori* in the stomach. The therapy of choice is at present a triple combination which consists of a so-called acid inhibitor, for example a proton pump inhibitor such as omeprazole, and two antibiotics, such as, for example, clarithromycin and amoxicillin. This triple therapy, however, is associated with disadvantages. As a result of differing diffusion properties, the three different substances, which should act together, do not uniformly reach the inflammatory foci caused by *H. pylori*. Thus, in order to achieve good healing results, very high doses, which are accompanied by serious side effects, are necessary. It is obvious that a triple therapy in other ways also generally has great disadvantages in comparison to the administration of two medicaments or even of only one medicament.

In EP-A-655 249, it has already been described that moenomycin antibiotics are also suitable as efficacious antibiotics for the control of *H. pylori* infections and thus for the treatment of gastric disorders such as, for example, gastric ulcers. The moenomycin antibiotics also display their action against *H. pylori* particularly advantageously on administration in combination with other antibiotics or other customary ulcer therapeutics or gastritis therapeutics, for example with antacids, $H_2$ receptor blockers, proton pump inhibitors, muscarinic receptor blockers or, for example, also with bismuth salts, such as, for example, bismuth nitrate, bismuth carbonate, bismuth salicylate or bismuth citrate.

The use of bismuth salts for the treatment of gastric ulcers has already been widely reported in the literature (see, for example, J. H. Walsh and W. L. Peterson, *New Eng. J. Med.* 333 (No. 15), 984–991, 1995). Bismuth compounds employed for this purpose are, in particular, basic bismuth compounds, inter alia, for example, bismuth subsalicylate, or also tripotassium dicitratobismuthate. The efficacy of the bismuth is, on the one hand, attributed to its astringent characteristics, on the other hand, however, direct effects of bismuth on *Helicobacter pylori* have also been described, such as, for example, the inhibition of the F1-ATPase from *H. pylori* (W. Beil and C. Birkholz, *Arch. Pharmacol.* 350, Suppl. R 1, 1994). The use of bismuth salts, in particular in the treatment of *Helicobacter pylori*-induced gastric ulcers, is therefore desirable.

Unfortunately, some disadvantages which are based on the chemical behavior of the bismuth salts stand in the way of the use of bismuth in the present form. Bismuth salts are very often poorly soluble in aqueous medium. So-called basic salts which contain the $BiO^{1+}$ ion and which are also designated as bismuth subsalts are formed in aqueous medium from the $Bi^{3+}$ ion. Basic bismuth salts of this type are deposited from aqueous solution, i.e. they form poorly soluble precipitates, and are thus not available or only limitedly available for biological action. The dissolved portions form colloids. As a result of these physicochemical properties, bismuth salts often have compositions which can only be stated approximately (see Römpps Chemie Lexikon (Römpp's Chemical Encyclopedia), 9th Edition, Georg Thieme Verlag, Stuttgart, N.Y., 1989, p. 439; DAB (Deutsches Arzneibuch (German Pharmacopeia)) 8, 526–530) and have a poor dosability, which makes the estimation of their effect additionally difficult.

The desired administration of bismuth salts in combination with, for example, acid inhibitors and antibiotics for the treatment of gastric disorders, such as ulcers and *H. pylori* infections, thus proves to be very problematic because of the solubility and pharmacodynamics of the bismuth salts, which differ from the acid inhibitors and antibiotics. There has therefore been no lack of attempts to simplify corresponding triple therapies to dual therapies or monotherapies. A large number of combinations of proton pump inhibitors, antibiotics and bismuth salts have been investigated without it in the end being possible, however, to excel the triple therapy. There is thus still a need for efficacious, simple-to-use and highly tolerable medicaments for the treatment of gastric disorders such as gastric ulcers or for the prophylaxis of stomach cancer.

Surprisingly, it has now been found that from the antibiotics of the moenomycin group and their derivatives, which are capable of salt formation at their acidic groups such as the phosphoric acid groups (or phosphoric ester groups) and/or the carboxylic acid groups, stable well-defined bismuth salts are obtainable which contain the antibiotic component present in the form of individual compounds or of mixtures and the bismuth in stoichiometric ratios. The action of these salts is clearly superior to the action of the pure antibiotics from the moenomycin group in the control of *Helicobacter pylori* or in the treatment and prophylaxis of gastric disorders, and they can be employed in the form of a dual therapy or even of a monotherapy. The discovery of well-defined bismuth salts of the antibiotics of the moenomycin group of this type is all the more surprising, as the conventional processes for obtaining such salts, such as precipitation from aqueous solution, dialyses or ion-exchanger applications, fail because of the already-discussed low solubility of the starting bismuth salts. They also fail because of the neutralization of the free acids of the antibiotics of the moenomycin group by basic bismuth, for example bismuth hydroxide.

The present invention thus relates to bismuth salts of antibiotics of the moenomycin group which antibiotics are present individually or as a mixture, and of their derivatives, and physiologically tolerable salts thereof. The bismuth salts according to the invention are stoichiometric compounds, i.e. defined chemical compounds of salt-like character which contain the acidic antibiotic(s) or derivatives thereof present in the new salts in anionic form and the bismuth in specific stoichiometric ratios. They are bismuth(III) salts, but they are not basic bismuth salts and do not have the disadvantages thereof explained above.

The stoichiometric ratio in which the bismuth and the antibiotic(s) or its/their derivatives are present in the salts according to the invention depends, for example, on the number of the acidic groups in the molecules of the antibiotic(s) and can be adjusted by means of the preparation conditions used, for example, by means of the molar ratio of the starting compounds employed in the preparation. A characteristic structural unit in antibiotics of the moenomycin group is the phosphoglyceric acid group or, as a part thereof, the doubly esterified phosphoric acid group, at whose free acid function salt formation can take place and which then represents a bismuth binding site. The stoichiometric ratio in the salts according to the invention can be indicated, for example, by indicating the number of moles or number of atoms of bismuth which is present per mole of the antibiotic(s), or it can also be indicated in a simple manner, for example, by indicating the phosphorus/bismuth molar ratio or atomic ratio, which is easy to determine. This ratio can be, for example, 1:1 or 1:2 (in the latter case this means that one bismuth atom is present per two phosphorus atoms or phosphoric acid groups in a salt according to the invention). The ratio, however, can also assume other values, also nonintegral values, for example if the salt according to the invention is derived from a mixture of two or more different antibiotics. If such a ratio, for example the ratio 1:1, is specified for the characterization of a salt according to the invention, then, of course, in macroscopic samples, such as are obtained, for example, in the industrial production of the salts according to the invention, the experimentally determined value can vary and differ slightly from the desired ideal value (for example 1:1), for example as a result of varying ratios of antibiotics or of by-components contained, and the indication of such a stoichiometric ratio for a substance according to the invention thus also includes, of course, ratios differing insignificantly therefrom.

Numerous antibiotics of the moenomycin group or their derivatives contain, in addition to the phosphoric acid group mentioned, one or, for example in the case of the derivatives, optionally also several carboxylic acid groups, at which salt formation with the bismuth can likewise take place. If the antibiotics, for example, contain a total of two acid functions in the molecule, such as, for example, the frequently occurring representatives having an acidic HO group in the phosphoric acid unit and having a COOH group, then they can bind two equivalents of bismuth or enter into two (salt) bonds with the bismuth. The third valency of the trivalent bismuth can then be saturated, for example, by a (salt) bond to additional anions (or anion equivalents), which are then contained in the salts according to the invention in addition to the antibiotics and the bismuth and which can originate, for example, from the starting bismuth salt used in the preparation of the salts according to the invention. The third valency of the bismuth, however, can also be saturated by a (salt) bond to a phosphoric acid group or carboxylic acid group in a second molecule of the antibiotic whereby finally a salt according to the invention results which contains two bismuth atoms per three molecules of the designated antibiotics or per three phosphorus atoms. Accordingly, also in other antibiotics and very generally in the compounds according to the invention valencies of the bismuth can be saturated by additional anions. Suitable additional anions of this type are, in particular, physiologically tolerable anions, for example chloride, bromide, nitrate, sulfate, phosphate, and other inorganic and organic anions which can be employed in pharmaceuticals, such as acetate, benzoate, citrate, tartrate, methanesulfonate, etc. In the salts according to the invention there can also be present more than one such additional anions in the form of a mixture.

Preferred bismuth salts according to the invention are those which, on account of their stoichiometric ratio bismuth: antibiotic, contain an additional physiologically tolerable anion for the neutralization of the bismuth, in particular one of the abovementioned anions. These salts can be regarded as a cationic complex of the bismuth and the antibiotic(s), for which the physiologically tolerable anion represents the negative counter ion. Bismuth salts according to the invention are particularly preferred in which the bismuth and the antibiotic present individually or as a mixture (or the bismuth and the phosphorus in the partially esterified phosphoric acid groups) are present in a molar ratio or atomic ratio of 1:1 (or approximately 1:1) and which contain an additional physiologically tolerable anion, it being possible for this anion to be a singly charged anion or an equivalent of a multiply charged anion. These particularly preferred salts can be represented by the formula $(A\,Bi)^+X^-$, in which A is an antibiotic of the moenomycin group or a derivative thereof present individually or as a mixture, which contains two acidic groups present in anionic form, and $X^-$ is a physiologically tolerable singly charged anion or an equivalent of a physiologically tolerable multiply charged anion.

The antibiotics of the moenomycin group are phosphoglycolipid antibiotics. Instead of the term antibiotics of the moenomycin group used here, in some cases the term phosphoglycolipid antibiotics is also used for these compounds. The present invention includes the bismuth salts of all antibiotics of this group. In particular, antibiotics of the moenomycin group are to be understood as meaning the actual moenomycins, i.e. moenomycin itself, and, for example, prasinomycin (obtainable from *Streptomyces prasinsus*), diumycin (macarbomycin, obtainable from *S. umbrinus* or *S. phaeochromogenes*), 11837 R.P. (obtainable from *S. viridans*), 8036 R.P. (quebemycin, obtainable from *S. canadiensis*), 19402 R.P. (obtainable from *S. peruviensis*), ensachomycin (obtainable from *S. cinnamonensis*), prenomycin (obtainable from *S. ambofaciens*), teichomycin (obtainable from *Actinoplanes teichomycelicus*), pholipomycin (obtainable from *S. lividoclavatus*) and others, which are all related phosphorus-containing acidic glycolipids. The bismuth salts of moenomycin itself are preferred. The individual antibiotics of the moenomycin group, again, are often complexes of several, structurally differing individual components. Individual components of moenomycin itself which may be mentioned, for example, are the moenomycins A, $A_{1.1}$, $A_{1.2}$, $B_1$, $B_2$, $C_1$, $C_2$, $C_3$, $C_4$ and others, in some cases differing notations being common, for example $A_{1/2}$. These individual components are obtainable from *Streptomyces bambergensis, S. ghanaensis, S. ederensis, S. geysirensis, S. prasinus*, or *S. lividoclavatus*. Preferred individual components of moenomycin itself with respect to the present invention are moenomycin A (formula I) and moenomycin $C_3$ (formula II) (in the formulae Ac is acetyl). A particularly preferred individual component is moenomycin A. With respect to further details of the antibiotics of the moenomycin group and especially moenomycin itself and its individual components and also other structural formulae, reference is made to the literature, for example to the article by G. Huber in "Antibiotics", ed. F. Hahn, Springer-Verlag, Berlin 1979, Vol. V, Part 1, pages 135–153, or to EP-A-655 249, which corresponds to U.S. patent application Ser. No. 08/348,815, which inasmuch are completely part of the present disclosure and are incorporated herein by reference.

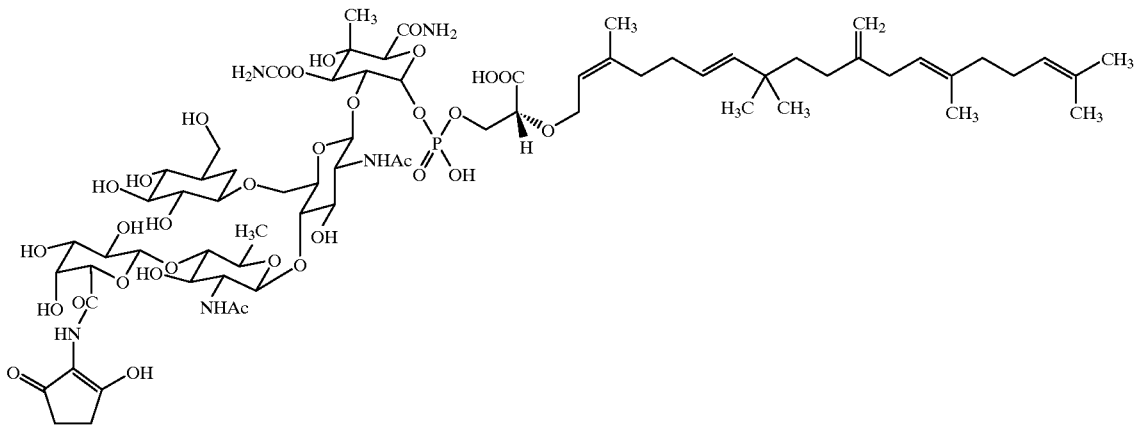

Formula I (moenomycin A)

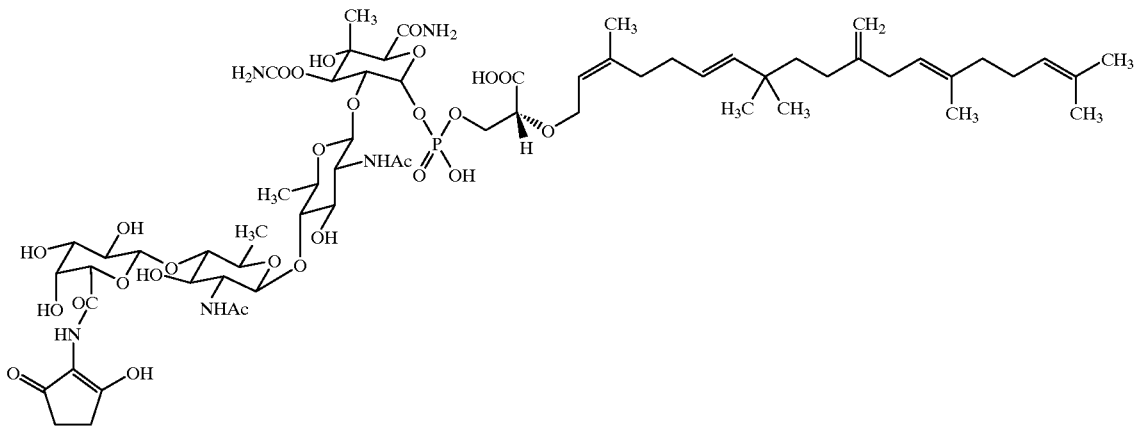

Formula II (moenomycin $C_3$)

Other components of moenomycin itself which form part of the present invention are represented, for example, by moenomycin $C_1$ (M. Heβler-Klintz et al., *Tetrahedron*, Vol. 49, No. 35, pp. 7667–7678, 1993, hereby incorporated by reference) and moenomycin $C_4$ (formula III).

or more individual antibiotics or starting mixtures, for example to obtain a specific profile of action.

The present invention also relates to the physiologically tolerable salts of the bismuth salts of the antibiotics of the moenomycin group. As salts there can already be regarded Formula III (moenomycin $C_4$)

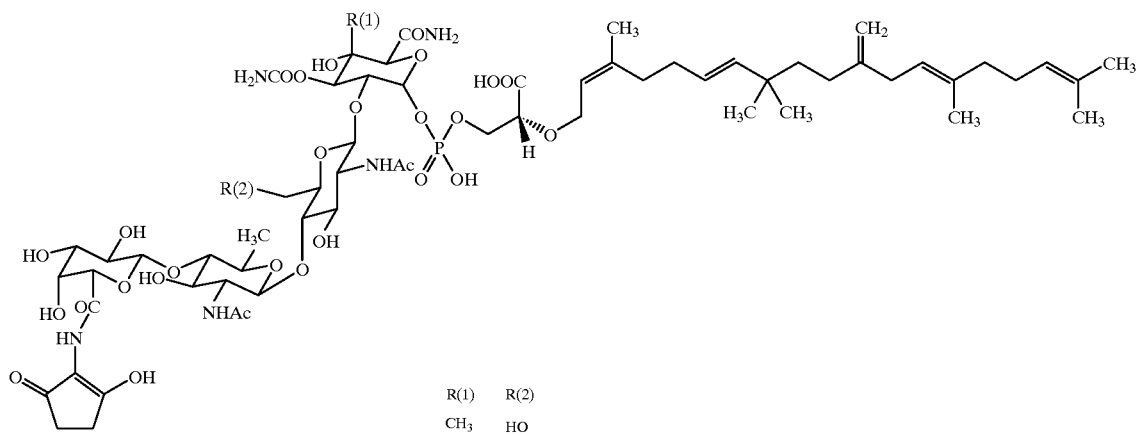

| | R(1) | R(2) |
|---|---|---|
| | $CH_3$ | HO |

Derivatives of antibiotics of the moenomycin group are to be understood as meaning, for example, structurally modified antibiotics which are suitable for the salt formation to be carried out according to the present invention and which are obtainable, for example, by chemical, biochemical or microbial conversion of functional groups, for example by hydrolyses, acylations or alkylations, but likewise, for example, also suitable degradation products of the antibiotics. The bismuth salts of the actual antibiotics of the moenomycin group are preferred, i.e. compounds in which no additional derivatization has been performed.

The antibiotics of the moenomycin group and likewise the actual moenomycins are in general obtained by fermentation of microorganisms and subsequent purification. Microorganisms employed are, for example, *Streptomyces bambergensis, S. ghanaensis, S. ederensis, S geysirensis, S. prasinus, S. lividoclavatus*, and others (G. Huber in "Antibiotics", ed. F. Hahn). In this case, the antibiotics are often obtained as mixtures or as complexes of individual components which may have varying compositions, and they are often also used in the form of such mixtures. If desired, the mixtures can be separated by customary methods into the pure or largely pure individual antibiotics or individual components, which have defined activities and are administered preferably. Correspondingly, the bismuth salts according to the invention can also be derived from mixtures of antibiotics of the moenomycin group or from individual antibiotics or from individual components of the complexes. The bismuth salts of all individual antibiotics of the moenomycin group and all possible combinations of more than one antibiotics of the moenomycin group are covered by the present invention. The mixtures can be derived from two or more individual antibiotics, it being possible for these to be individual components of a specific antibiotic, for example of moenomycin itself, and/or for these to belong to different antibiotics of the moenomycin group. Mixtures of antibiotics contained in the salts according to the invention can have the composition in which they are obtained during their synthesis or purification or they can, for example, also be prepared by specific mixing of two the compounds according to the invention illustrated above which contain additional anions such as chloride, bromide, nitrate etc. If a bismuth salt according to the invention contains, as an additional anion, an anion of a polybasic acid, for example sulfuric acid or citric acid, it is also possible for only one of these acid functions to be neutralized by bismuth and the second or others to be completely or partially present, for example, as metal salts or ammonium salts. Acidic groups which are present in the molecule of the antibiotic or which are produced by derivatization, which are not neutralized by salt formation with the bismuth, can also be present as metal salts or ammonium salts, or basic groups present in the antibiotics or produced by derivatization, for example by hydrolysis of amide groups to amino groups, can be present as acid addition salts. Suitable metal salts are, in particular, alkali metal salts and alkaline earth metal salts, for example sodium, potassium, calcium or magnesium salts. Ammonium salts can be derived from ammonia and from organic amines. Acid addition salts can be derived, for example, from hydrochloric acid, hydrobromic acid, nitric acid, sulfuric acid, phosphoric acid or other inorganic and organic acids which can be employed in pharmaceuticals, such as acetic acid, benzoic acid, citric acid, tartaric acid, methanesulfonic acid and others. The salts can be prepared by the customary processes known to the person skilled in the art. Internal salts (betaines) are also covered by the invention. The present invention furthermore relates to solvates of the bismuth salts of antibiotics of the moenomycin group, for example with water or alcohols, and other derivatives, for example esters, and active metabolites of the compounds according to the invention.

The bismuth salts of the antibiotics of the moenomycin group according to the invention are obtainable, for example, by reacting the antibiotic(s) of the moenomycin group or in particular its/their customarily used salts with a bismuth salt in a solvent or dispersant. This preparation process also is a subject of the present invention. The antibiotics in this case are customarily employed in the form of alkali metal salts or ammonium salts, preferably in the form of the sodium, potassium or ammonium salts, which are adequately soluble in organic solvents. Solvents used for the reaction are preferably organic solvents, however organic solvents containing water can also be used. Preferably, the antibiotics (or their starting salts) and the starting bismuth salt are employed in the form of solutions, particularly preferably, especially the starting bismuth salt is employed in the form of a solution in an organic solvent. In the reaction, defined bismuth salts of stoichiometric composition of the antibiotics of the moenomycin group are formed, which are often poorly soluble in organic solvents and are already deposited from the reaction mixture in largely pure form, and which can be separated off in a simple manner or which otherwise can be isolated according to customary methods and, if desired, further purified.

The composition of the products according to the invention thus obtainable and the proof that they are not physical mixtures of bismuth compounds with the antibiotics, but homogeneous chemical compounds of stoichiometric composition which contain the bismuth, the antibiotics and optionally, for example, an additional anion can be determined by the customary analytical processes known to the person skilled in the art. The content of bismuth and other elements can be determined in a known manner, for example by elemental analysis. The antibiotic content of a salt according to the invention can be demonstrated and identified, for example, by recording NMR spectra.

NMR spectroscopy also allows an unequivocal conclusion that defined bismuth salt formation takes place on certain acidic groups of the antibiotic. For example, a comparison of the $^1$H- and $^{13}$C-NMR signals of a bismuth salt according to the invention with that of the corresponding sodium salt of the antibiotic used as a starting material for its synthesis shows that specific signals are shifted in a characteristic manner, in particular those of atoms which are adjacent to the acidic centers at which the bismuth salt formation takes place (cf. NMR data in Example 1). This proves that the substances according to the invention are novel, well-defined compounds and confirms their structure.

X-ray spectrometric processes such as X-ray fluorescence analysis and moreover scanning transmission electron microscopy, which can be coupled with energy-dispersive X-ray microanalyses, are also highly suitable. Beside the detection of the elements, for example of the bismuth or of the phosphorus, these analytical methods allow the determination of the ratio of the elements present in different, extremely small sample sites, such as, for example, the ratio of bismuth to phosphorus, or, for example, to chlorine, sodium and other elements. The products according to the invention are also homogeneous according to energy-dispersive X-ray microanalysis, the concentration ratio of, for example, bismuth to phosphorus is always constant, a compound of stoichiometric composition is thus present.

As already stated, preferred solvents in the preparation of the bismuth salts according to the invention are organic solvents. However, aqueous-organic solvents can also be employed in which the water content should be so low that substantially no hydrolysis of the bismuth salt employed as a starting material occurs under the reaction conditions. The permissible water content depends on the individual case. Suitable organic solvents are, for example, lower alcohols, in particular methanol and ethanol, ethylene glycol monomethyl ether, glycols, such as, for example, ethylene glycol or 1,2-propylene glycol, dimethyl sulfoxide (DMSO), dimethylformamide, ethers such as dioxane, tetrahydrofuran, ethylene glycol ethers, and mixtures of these solvents and other solvents. In particular, lower alcohols are preferred in which the antibiotics of the moenomycin group or their salts dissolve well, such as methanol or ethanol.

For the preparation of the compounds according to the invention, the antibiotics of the moenomycin group are preferably initially introduced as a solution, for example in methanol, having a concentration from, customarily, 0.1 to 10% by weight, preferably from 1 to 5% by weight. As already stated, the antibiotics can be employed in the bismuth salt formation in the form of mixtures of several antibiotics or in the form of complexes of one antibiotic, for example of moenomycin, or as individual components, for example as moenomycin A or $C_3$, where, as also already stated, salts such as, for example, the sodium salts or ammonium salts are customarily employed. Suitable bismuth(III) salts are in particular salts of the $Bi^{3+}$ ion, which dissolve well in organic solvents, such as, for example, bismuth chloride ($BiCl_3$), bismuth nitrate ($Bi(NO_3)_3$), bismuth bromide ($BiBr_3$) and others. The employed solution of bismuth(III) salt in an organic solvent customarily has a concentration from 0.01 to 1 mol per liter, preferably from 0.1 to 0.5 mol per liter. The bismuth solution is preferably metered into the solution of the antibiotic, and while doing this often, but of course depending on the individual case, the salt according to the invention is already deposited. The molar ratio of the reactants can be varied within a wide range. Preferably, equimolar ratios are used, in particular if the preferred bismuth salts are to be prepared which contain the antibiotic (or the phosphorus) and the bismuth in the molar ratio or atomic ratio 1:1. As already stated, various bismuth salts can be obtained depending on the preparation conditions used.

In general, the reaction of the bismuth salts with the antibiotics is carried out in the temperature range from $-20°$ C. to $80°$ C., preferably in the range from $10°$ C. to $30°$ C. The reaction is advantageously carried out by slowly metering in in the course of, in general, 20 minutes to 2 hours. In a more rapid procedure, if the product is deposited, so-called inclusions can adversely affect the purity of the product. If the product is poorly soluble in the solvent employed, then, for isolation of the product, the precipitate formed in the deposition can be separated off by centrifuging or filtering and, if desired, purified, for example by suspending in a suitable organic solvent and centrifuging or filtering again. If the product is readily soluble, such that it remains in solution, completely or to a relatively large extent, then according to the customary procedures the solvent can initially be partially or completely removed, for example by vacuum distillation and/or freeze drying, and/or a solvent can be added in which the product is poorly soluble, and the product deposited can then be separated off. For isolation, however, chromatographic processes can also be employed. After drying, the product is obtained as a white or pale powder, which in general is highly soluble in water and soluble in DMSO, but poorly soluble in many other organic solvents. If desired, the product can additionally be purified by customary processes, for example by reprecipitation or chromatography.

Furthermore, bismuth salts according to the invention which contain an additional anion can in particular be obtained, for example, by ion-exchange processes. Thus, for example, a bismuth salt according to the invention which contains a specific anion can be converted by anion exchange according to customary procedures, for example by reaction with a salt or an acid in a solvent or by chromatography, into another bismuth salt according to the invention which contains another physiologically tolerable anion as an additional anion.

The biological and therapeutic actions of the antibiotics of the moenomycin group, in particular of the moenomycins themselves, and the advantages of the use of these antibiotics in the therapy and prophylaxis of gastric disorders are described in detail in EP-A-655 249. The bismuth salts according to the invention actually even excel the advantageous antibacterial and healing-promoting properties of the moenomycins to a considerable extent. This is seen both in in vitro experiments and in vivo. As detailed further below, the action of the bismuth salt of moenomycin A, for example, is clearly superior to the action of moenomycin A (as a sodium salt) already in in vitro experiments. The moenomycin and the bismuth act synergistically. In the form of the salts according to the invention, both components can reach the inflammatory focus together by diffusion and display their actions there, which in the case of the customary administration of an antibiotic and of a separate bismuth salt is not possible or only possible to a very much smaller extent.

A crucial advantage of the compounds according to the invention is that, because of the higher activity of the compounds according to the invention, smaller doses can be administered in order to achieve the therapeutic aim, for example the eradication of *H. pylori*, and that fewer side effects are associated therewith. The wide and high efficacy of the bismuth salts according to the invention allows their use alone as an antimicrobial agent instead of two antibiotics in conventional therapy. Triple therapy can thereby be simplified to dual therapy, in which beside the bismuth salt according to the invention, for example, only an antacid (for example omeprazole, lansoprazole, pantoprazole or others) is administered. As a result, the patient is treated more gently and costs are lowered. The eradication of *H. pylori* is even possible using the bismuth salts according to the invention on its own without any additional medication. This monotherapy is far superior to other ulcer therapies with respect to simplicity, tolerability and cost effectiveness.

The bismuth salts of antibiotics of the moenomycin group according to the invention and their physiologically tolerable salts can thus be used in animals, preferably in mammals, and in particular in man, as pharmaceuticals per se, in mixtures with one another or in the form of pharmaceutical preparations. The present invention also relates to the bismuth salts according to the invention and their physiologically tolerable salts for use as pharmaceuticals, to their use in the therapy and prophylaxis of ulcers generally, such as, for example, duodenal ulcer or peptic ulcer, of gastric disorders, in particular gastric ulcers or gastritis, in the prophylaxis of stomach cancer, and generally in the control of *Helicobacter pylori*, and to their use for the production of medicaments for the uses mentioned. The present invention furthermore relates to pharmaceutical preparations which, as active constituent, contain an efficacious dose of at least one bismuth salt according to the invention and/or a physiologically tolerable salt thereof in addition to customary, pharmaceutically innocuous excipients and/or auxiliaries. The pharmaceutical preparations normally contain 0.5 to 95 percent by weight of the bismuth salts according to the invention and/or their physiologically tolerable salts. The pharmaceutical preparations can be prepared in a manner known per se. For this purpose, the bismuth salts according to the invention and/or their physiologically tolerable salts are brought, together with one or more solid or liquid pharmaceutical excipients and/or auxiliaries and, if desired, in combination with other pharmaceutically active compounds, into a suitable administration form or dosage form which can then be used as a pharmaceutical in human medicine or veterinary medicine. These pharmaceuticals are mainly intended for oral administration.

The bismuth salts according to the invention and their physiologically tolerable salts can also be combined with other pharmaceutically active compounds to achieve an advantageous therapeutic action, in particular with one or more further pharmaceutically active compounds for the treatment of gastric disorders or ulcers. For the therapeutic and prophylactic uses mentioned, suitable additional active compounds derive, for example, from the antacids group, such as, for example, sodium bicarbonate, aluminum hydroxide, magnesium hydroxide, magnesium trisilicate, aluminum magnesium silicate hydrate, aluminum sodium carbonate dihydroxide, magnesium carbonate, calcium carbonate or hydrotalcite. Other suitable additional active compounds derive from the $H_2$ receptor blocker group, such as, for example, famotidine, nizatidine, roxatidine acetate, ranitidine or cimetidine. Other suitable additional active compounds are muscarinic receptor blockers such as propantheline bromide, pirenzipine, or other anti-ulcer agents such as omeprazole, lansoprazole, pantoprazole, misoprostol, or also additional bismuth salts such as bismuth nitrate, bismuth carbonate, bismuth salicylate or bismuth citrate. Other additional active compounds suitable for the therapy according to the invention belong to the antibiotics group, such as, for example, tetracycline, metronidazole, amoxycillin, nisin, clarithromycin, imipenem or amikacin. A preferred combination contains the bismuth salts according to the invention together with a proton pump inhibitor such as, for example, omeprazole, lansoprazole, pantoprazole or others. It may also be advantageous to combine the bismuth salts according to the invention with several of the abovementioned additional active compounds or with further active compounds for other indications. The administration of the components of the combinations mentioned can be carried out together or in separate form, and it can be carried out in a single administration or alternatively performed sequentially.

Suitable pharmaceutical administration forms for the administration of the bismuth salts according to the invention are, for example, capsules, for example hard or soft capsules, tablets, pastilles, lozenges, roll treatments (i.e. treatments in which the medicine taken is distributed in the stomach by the patient lying some minutes on the back, then some minutes on the side, then some minutes on the front, etc.), dispersible powders and granules, microbeads, solutions or suspensions, in particular aqueous solutions and suspensions, emulsions, syrups and elixirs, and similar forms known in the art. Solid administration forms are preferred, in particular those which release the active principle in the stomach.

The pharmaceutical preparations can be prepared by the appropriate methods known in the art for the production of pharmaceutical preparations using pharmaceutically acceptable, nontoxic auxiliaries and excipients. As excipients, tablets for oral administration can contain, for example, inert extenders (such as, for example, sodium chloride, lactose, calcium phosphate or sodium phosphate), granulating agents or disintegrants (for example potato starch, alginic acid), binders (such as, for example, starch, gelatin or gum arabic) and lubricants (such as, for example, magnesium stearate, stearic acid or talc). The tablets can be uncoated or they can be coated by means of the known techniques in order to delay dissolution and absorption in the stomach and thus to give a lasting action over a relatively long period of time. Thus, for example, a release-delaying substance such as, for example, glyceryl monostearate or glyceryl distearate can be employed. In hard gelatin capsules for oral administration, the active compound can be mixed, for example, with an inert solid extender, for example calcium phosphate or kaolin, in soft gelatin capsules the active compound can be mixed, for example, with an aqueous medium, for example water, or an oily medium, for example peanut oil, liquid paraffin or olive oil. The excipients and/or auxiliaries suitable for the desired pharmaceutical formulation are familiar to the person skilled in the art on the basis of his expert knowledge. As auxiliaries there may be mentioned, for example, antioxidants, dispersants, emulsifiers, solubilizers, stabilizers, flavorings, sweeteners, colorants, preservatives, agents for achieving a depot effect, buffer substances, etc.

The dose to be administered of the bismuth salts according to the invention or of their physiologically tolerable salts depends on the individual case and is to be adapted to the conditions of the individual case for an optimum action as usual. Thus it depends, of course, on the frequency of administration and on the potency and duration of action of the compounds employed in each case for therapy or prophylaxis, but also on the nature and severity of the disease to be treated and on the sex, age, weight, state of health, nutrition, individual responsiveness of the human or animal to be treated, on interactions with other pharmaceuticals and on whether treatment is acute or prophylactic. Customarily, the daily dose in the case of oral administration of a pharmaceutical preparation to a human weighing approximately 75 kg is 5 mg to 5 g per person per day, preferably 50 mg to 2 g per person per day. The dose can be administered in the form of an individual dose or subdivided into several, for example, two, three or four, individual doses.

Apart from as pharmaceutically active compounds, the bismuth salts according to the invention can also be used, as already mentioned above, as intermediates for the production of other pharmaceutically active compounds. They can furthermore be employed as auxiliaries in biochemical or microbiological investigations or in diagnostic procedures, for example in in vitro diagnoses.

EXAMPLES

Example 1

Bismuth salt of moenomycin A in the chloride form (Formula: $(C_{69}H_{106}BiN_5O_{34}P)^+$, counterion: $Cl^-$; MW 1825)

50 g of moenomycin A sodium salt were dissolved in 2 L of methanol and treated with stirring with 9.6 g of $BiCl_3$ in 100 ml of methanol for 2 hours at room temperature. After gentle stirring for a further 15 minutes, the resulting white precipitate was washed several times with 2 L of methanol each by stirring the precipitate with a glass rod and collecting the undissolved bismuth salt of moenomycin A by centrifuging. After drying in vacuo, 28 g of product were obtained which after grinding and sieving was employed for the biological investigations. The product obtained was characterized, inter alia, by the following analyses.

a) $^1H$- and $^{13}C$-NMR

Chemical shifts (in ppm) of the moenomycin A bismuth salt in the chloride form obtained according to Example 1 and of the moenomycin A sodium salt as a comparison are shown (in $d_6DMSO$)

| Molecule position (see Formula Ia below) | Bi salt, chloride form $^1H$ | Na salt $^1H$ | Bi salt, chloride form $^{13}C$ | Na salt $^{13}C$ |
|---|---|---|---|---|
| 1 | 4.07/3.94 | 4.07/3.83 | 65.42 | 64.78 |
| 2 | 5.33 | 5.32 | 121.66 | 123.51 |
| 3 | — | — | 138.73 | 136.84 |
| 4 | 2.06 | 2.03 | 31.80 | 31.96 |
| 5 | 2.05 | 2.02 | 30.70 | 30.88 |
| 6 | 5.25 | 5.24 | 125.23 | 125.43 |
| 7 | 5.36 | 5.35 | 139.80 | 139.79 |
| 8 | — | — | 35.07 | 35.19 |
| 9 | 1.33 | 1.33 | 40.86 | 40.91 |
| 10 | 1.86 | 1.85 | 30.61 | 30.68 |
| 11 | — | — | 149.15 | 149.21 |
| 12 | 2.66 | 2.65 | 34.39 | 34.47 |
| 13 | 5.12 | 5.11 | 121.66 | 121.75 |
| 14 | — | — | 135.69 | 135.81 |
| 15 | 1.98 | 1.98 | 39.08 | 39.22 |
| 16 | 2.05 | 2.05 | 26.01 | 26.08 |
| 17 | 5.07 | 5.06 | 123.96 | 124.05 |
| 18 | — | — | 130.56 | 130.70 |
| 19 | 1.63 | 1.63 | 25.34 | 25.48 |
| 20 | 1.55 | 1.55 | 17.37 | 17.53 |
| 21 | 1.57 | 1.57 | 15.62 | 15.71 |
| 22 | 4.66 | 4.65 | 108.58 | 108.70 |
| 23 | 0.94 | 0.93 | 27.02 | 27.11 |
| 24 | 0.94 | 0.93 | 27.02 | 27.11 |
| 25 | 1.70 | 1.67 | 23.20 | 23.28 |
| 26 | — | — | *) | 173.68 |
| 27 | 4.03 | 3.64 | 77.69 | 80.89 |
| 28 | 3.85 | 3.99/3.75 | 65.23 | 67.25 |
| A-NH | 8.66 | 7.47 | — | — |
| A1 | — | — | broad | 193.37 |
| A2 | — | — | *) | 109.67 |
| A3 | — | — | broad | 193.37 |
| A4 | broad | 2.00 | *) | 30.88 |
| A5 | broad | 2.00 | *) | 30.88 |
| B1' | 4.41 | 4.33 | 102.87 | 103.24 |
| B2' | 3.41 | 3.38 | 69.79 | 70.24 |
| B3' | 3.41 | 3.37 | 72.48 | 72.98 |

| Molecule position (see Formula Ia below) | Bi salt, chloride form $^1$H | Na salt $^1$H | Bi salt, chloride form $^{13}$C | Na salt $^{13}$C |
|---|---|---|---|---|
| B4' | 3.93 | 3.92 | 69.08 | 69.46 |
| B5' | 4.26 | 3.94 | 74.31 | 75.36 |
| B5'-C' | — | — | 169.37 | 167.03 |
| C1' | 4.51 | 4.66 | 101.09 | 100.98 |
| C2' | 3.52 | 3.52 | 55.50 | 55.63 |
| C2'-NH | 7.81 | 8.08 | — | — |
| C2'-C' | — | — | 169.44 | 170.03 |
| C2'-Ac | 1.88 | 1.90 | 22.94 | 22.97 |
| C3' | 3.54 | 3.48 | 71.66 | 72.89 |
| C4' | 3.21 | 3.15 | 83.71 | 84.02 |
| C5' | 3.52 | 3.48 | 70.32 | 70.73 |
| C5'-Me | 1.33 | 1.31 | 17.37 | 17.53 |
| D1' | 4.35 | 4.37 | 102.64 | 102.88 |
| D2' | 2.97 | 2.96 | 73.41 | 73.49 |
| D3' | 3.25 | 3.26 | 76.67 | 76.69 |
| D4' | 3.04 | 3.01 | 70.33 | 70.24 |
| D5' | 3.21 | 3.21 | 76.67 | 77.21 |
| D6' | 3.70/3.44 | 3.71/3.44 | 61.24 | 61.52 |
| E1' | 4.51 | 4.46 | 101.09 | 101.53 |
| E2' | 3.37 | 3.55 | 55.02 | 55.01 |
| E2'-NH | 7.41 | 7.61 | — | — |
| E2'-C' | — | — | 169.03 | 169.81 |
| E2'-Ac | 1.82 | 1.82 | 23.10 | 23.03 |
| E3' | 3.59 | 3.53 | 71.83 | 72.79 |
| E4' | 3,35 | 3.35 | 80.27 | 79.67 |
| E5' | 3.41 | 3.38 | 73.83 | 72.03 |
| E6' | 3.97/3.54 | 3.99/3.44 | 67.39 | 68.28 |
| F1' | 5.67 | 5.75 | 93.60 | 93.69 |
| F2' | 3.43 | 3.38 | 76.63 | 77.21 |
| F3' | 4.91 | 4.90 | 73.85 | 74.15 |
| F3'-NH$_2$ | 6.25 | 6.36 | — | — |
| F3'-C' | — | — | 156.15 | 156.53 |
| F4' | — | — | 72.60 | 72.53 |
| F4'-Me | 1.10 | 1.06 | 16.21 | 16.04 |
| F5' | 4.21 | 4.28 | 71.61 | 71.71 |
| F5'-NH$_2$ | 7.42/7.02 | 7.49/7.29 | — | — |
| F5'-C' | — | — | 171.79 | 171.80 |

*)These signals cannot be assigned unequivocally.

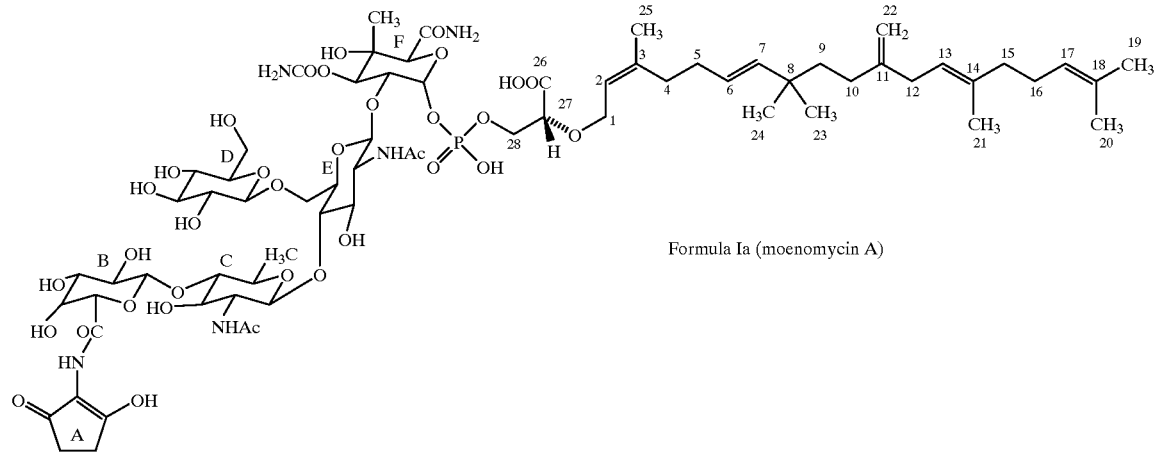

Formula Ia (moenomycin A)

b) Electron-dispersive X-ray Microanalysis (EDX)

Ten powder agglomerates were investigated by means of EDX. The diameter of the sample sites investigated was in each case about 50 nm. Bismuth was detected at each site. The atomic ratio bismuth: phosphorus was always 1:1, i.e. the bismuth is homogeneously and stoichiometrically incorporated into the organic powder particles. Beside the bismuth and phosphorus (and also chlorine, carbon and oxygen), small amounts of sodium were detected in locally differing concentrations.

The supernatant from the moenomycin A/bismuth chloride precipitation was treated with 100 ml of DMSO, concentrated in vacuo to 200 ml and applied to a column packed with 20 L of Fractogel TSK HW-40. It was fractionally eluted using DMSO/methanol (1:1). The eluate fractions containing the bismuth salt of moenomycin A were combined and freed from the solvent by vacuum distillation and by freeze-drying. They afforded a further 21 g of the bismuth salt of moenomycin A in the chloride form, which was identical to the product first obtained.

Example 2

Bismuth salt of moenomycin A in the nitrate form (Formula: $(C_{69}H_{106}BiN_5O_{34}P)^+$, counterion: $NO_3^-$; MW 1851.5)

163 mg of moenomycin A sodium salt were dissolved in 4 ml of methanol and treated with stirring with a solution of 48.5 mg of bismuth(III) nitrate pentahydrate in 200 μl of DMSO. A precipitate resulted, which was purified by suspending three times in methanol, centrifuging and separating off the supernatant. After drying the precipitate in vacuo, 112 mg of bismuth salt of moenomycin A in the nitrate form were obtained. Electron-dispersive X-ray microanalysis was carried out as in Example 1 and gave corresponding results, but no chlorine content.

According to the above Examples, the following bismuth salts of moenomycin antibiotics can also be obtained:

Moenomycin $A_{1,2}$ bismuth salt in the chloride form (Formula: $(C_{68}H_{104}BiN_5O_{34}P)^+$, counterion: $Cl^-$; MW 1811)

Moenomycin $C_1$ bismuth salt in the chloride form (Formula: $(C_{62}H_{94}BiN_5O_{28}P)^+$, counterion: $Cl^-$; MW 1632.8)

Moenomycin $C_3$ bismuth salt in the chloride form (Formula: $(C_{63}H_{96}BiN_5O_{28}P)^+$, counterion: $Cl^-$; MW 1646.9)

Moenomycin $C_4$ bismuth salt in the chloride form (Formula: $(C_{63}H_{96}BiN_5O_{29}P)^+$, counterion: $Cl^-$; MW 1662.9)

Biological Investigations

Antibacterial activity of the bismuth salts of antibiotics of the moenomycin group against *Helicobacter pylori* was assayed. *Helicobacter pylori* was precultured at 35° C. on tryptic soy-agar (+5% defibrinated sheeps' blood,+actidione 500 μg/ml) under microaerophilic conditions (Anaerocult, Merck) in a $CO_2$ atmosphere (8–10% $CO_2$) for 5 days. For the actual experiment, the grown cultures were removed completely from the preculture plate using a cotton swab, suspended in 0.9% strength NaCl solution and adjusted using McFarland standard to a microorganism density of $3 \times 10^8$ cfu/ml. The in vitro activity of the test substances was determined by the agar dilution method using Columbia agar (+5% defibrinated sheeps' blood,+actidione, 500 μg/ml) as test medium. The agar plates, which contained various concentrations of test substance (0.002 to 128 μg/ml), were inoculated in a punctiform manner (multipoint inoculator, Denley) with the adjusted microorganism suspensions. Incubation was carried out under microaerophilic conditions (see above). After 5 days at 35° C., the lowest substance concentration was determined at which colony formation was not detectable visually, and defined as the minimum inhibitory concentration (MIC). Like the bismuth salts, the corresponding sodium salts were investigated for comparison.

Results: Minimum inhibitory concentration (μg/ml)

| Microorganism | Moenomycin A sodium salt (Comparison) | Moenomycin A bismuth salt, chloride form (Example 1) |
|---|---|---|
| *H. pylori* P 42 | 2 | 0.5 |

What is claimed is:

1. A composition of matter, comprising a bismuth salt of an antibiotic of the moenomycin group or a physiologically tolerable salt thereof, wherein said antibiotic of the moenomycin group is present individually, or as a mixture, or as a derivative thereof.

2. The composition of matter of claim 1, wherein the antibiotic is one or more of moenomycin, prasinomycin, diumycin, 11837 R.P., 8036 R.P., 19402 R.P., ensachomycin, prenomycin, teichomycin or pholipomycin.

3. The composition of matter of claim 1, wherein the bismuth salt is derived from at least one of the components of moenomycin.

4. The composition of matter of claim 3, wherein the antibiotic is at least one of moenomycin A or moenomycin $C_3$.

5. The composition of matter of claim 1, wherein said bismuth salt of an antibiotic of the moenomycin group further comprises a physiologically tolerable anion.

6. The composition of matter of claim 4, wherein said bismuth salt of an antibiotic of the moenomycin group further comprises a physiologically tolerable anion.

7. The composition of matter of claim 1, wherein the bismuth and the antibiotic are present in a molar ratio of approximately 1:1.

8. A method of preparing the composition of matter of claim 1, comprising reacting at least one antibiotic of the moenomycin group or a salt thereof with a bismuth salt in a solvent or dispersant.

9. A pharmaceutical composition, comprising a bismuth salt of claim 1 or a physiologically tolerable thereof, and a pharmaceutically tolerable excipient.

10. A pharmaceutical composition of claim 9, further comprising an active compound for the treatment of gastric disorder or ulcers.

11. A method for treating ulcers, gastric disorders, gastric ulcers, or gastritis, comprising administering to a host in need thereof an effective amount of a bismuth salt of claim 1 or a physiologically tolerable salt thereof.

12. A pharmaceutical composition for the control of *Helicobacter pylori*, comprising an effective amount of at least one bismuth salt of claim 1 or of a physiologically tolerable salt thereof, together with a pharmaceutically tolerable excipient or auxiliary.

13. A method for controlling *Helicobacter pylori*, comprising administering to a host in need thereof an effective amount of a bismuth salt of claim 1 or a physiologically tolerable salt.

14. A pharmaceutical composition for the reduction of the risk of stomach cancer in which *H. pylori* is a causative factor, comprising an efficacious amount of at least one bismuth salt of claim 1 or of a physiologically tolerable salt thereof, together with a pharmaceutically tolerable excipient or auxiliary.

15. A method for reducing the risk of stomach cancer in which *H. pylori* is a causative factor, comprising administering to a host in need thereof an effective amount of a bismuth salt of claim 1 or a physiologically tolerable salt thereof.

16. A pharmaceutical composition for treating ulcers, gastric disorders, gastric ulcers, or gastritis, comprising an effective amount of at least one bismuth salt of claim 1 or of a physiologically tolerable salt thereof, together with a pharmaceutically tolerable excipient or auxiliary.

17. A method for controlling conditions in which *H. pylori* is a causative factor, comprising administering an effective amount of a bismuth salt of claim 1 or a physiologically tolerable salt thereof to a host at risk for developing symptoms of such conditions.

18. A pharmaceutical composition for controlling conditions in which *H. pylori* is a causative factor, comprising an effective amount of at least one bismuth salt of claim 1 or of a physiologically tolerable salt thereof, together with a pharmaceutically tolerable excipient or auxiliary.

* * * * *

UNITED STATES PATENT AND TRADEMARK OFFICE
CERTIFICATE OF CORRECTION

PATENT NO. : 6,077,830
DATED : June 20, 2000
INVENTOR(S) : Laszlo Vertesy et al.

It is certified that error appears in the above-indentified patent and that said Letters Patent is hereby corrected as shown below:

Claim 9, Column 18, line 19, after "tolerable", insert --salt--.

Claim 10, Column 18, line 23, "disorder" should read --disorders--.

Signed and Sealed this

Tenth Day of April, 2001

Attest:

NICHOLAS P. GODICI

Attesting Officer           Acting Director of the United States Patent and Trademark Office

UNITED STATES PATENT AND TRADEMARK OFFICE
CERTIFICATE OF CORRECTION

PATENT NO.: 6,077,830

DATED: June 20, 2000

INVENTORS: Laśzlo Vértesy et al.

It is certified that an error appears in the above-identified patent and that said Letters Patent is hereby corrected as shown below:

Claim 9, Column 18, line 19, after "tolerable", insert --salt--.

Claim 10, Column 18, line 23, "disorder" should read --disorders--.

Signed and Sealed this

First Day of May, 2001

Attest:

NICHOLAS P. GODICI

Attesting Officer     Acting Director of the United States Patent and Trademark Office